United States Patent
Ono

[11] Patent Number: 6,053,862
[45] Date of Patent: Apr. 25, 2000

[54] ILLUMINATION OPTICAL SYSTEM

[75] Inventor: Katsuya Ono, Hino, Japan

[73] Assignee: Olympus Optical Co., Ltd., Tokyo, Japan

[21] Appl. No.: 09/124,006

[22] Filed: Jul. 29, 1998

[30] Foreign Application Priority Data

Aug. 1, 1997 [JP] Japan .................................. 9-207445

[51] Int. Cl.[7] .................................................. A61B 1/07
[52] U.S. Cl. ........................ 600/177; 600/182; 359/619
[58] Field of Search .................................. 600/176, 177, 600/116; 362/32; 359/619, 621; 385/117, 118, 119

[56] References Cited

U.S. PATENT DOCUMENTS

| | | | |
|---|---|---|---|
| 4,802,460 | 2/1989 | Ohkuwa | 600/177 |
| 5,282,088 | 1/1994 | Davidson | 359/664 |
| 5,307,205 | 4/1994 | Ludwig, Jr. et al. | 359/453 |
| 5,354,322 | 10/1994 | Miyano | 607/88 |
| 5,384,467 | 1/1995 | Plimon | 250/554 |
| 5,837,346 | 11/1998 | Langille et al. | 359/453 |

FOREIGN PATENT DOCUMENTS

| | | |
|---|---|---|
| 55-136031 | 10/1980 | Japan . |
| 63-239415 | 10/1988 | Japan . |
| 1-198717 | 8/1989 | Japan . |
| 08122661 | 5/1996 | Japan . |

*Primary Examiner*—John P. Leubecker
*Attorney, Agent, or Firm*—Pillsbury Madison & Sutro LLP

[57] ABSTRACT

An illumination optical system has a diffusion member including a number of nearly spherical members which are diminutive in size and transparent and a transparent medium whose refractive index is higher than that of air and different from that of the nearly spherical members and which holds the nearly spherical members, on the exit end face of a light conducting device for introducing illumination light. In this way, a visual field can be efficiently illuminated.

15 Claims, 8 Drawing Sheets

ILLUMINATION OPTICAL SYSTEM

BACKGROUND OF THE INVENTION

1. Field of the Invention

This invention relates to an illumination optical system which is capable of efficiently changing the distribution of illumination light having directivity, for example, from a light guide or surface illuminant.

2. Description of Related Art

Light guides have been widely used in illumination optical systems for endoscopes. Although the endoscopes have various field angles in accordance with their specifications, they are generally wide-angle and those having field angles of about 100 to 140° are chiefly used. On the other hand, in the illumination optical systems for endoscopes, light guides with a numerical aperture of approximately 0.6 are often used. Since this is on the order of 70° in terms of an angle of view, it follows that the radiation angle of illumination light is smaller than the field angle of the endoscope. Thus, in order to increase the radiation angle of illumination light from a light guide, many endoscopes are provided with a variety of optical members at the exit end faces of light guides.

For example, in each of Japanese Patent Preliminary Publication Nos. Sho 63-239415 and Hei 8-122661, a negative lens is placed, as an optical member for increasing the radiation angle of illumination light, at the exit end of the light guide. In Japanese Patent Preliminary Publication No. Hei 1-198717, frosted glass is used as another optical member. Further, Japanese Patent Preliminary Publication No. Sho 55-136031 discloses an optical system in which cylindrical or ball lenses are arranged in front of the exit end face of the light guide.

However, illumination lenses disclosed in Sho 63-239415 or Hei 8-122661 are negative lenses, and thus must have considerable thicknesses in order to completely pass a light beam through their periphery as well. Consequently, the outside diameter of the lens will be increased and an intention of reducing the diameter of the endoscope will be defeated. Furthermore, since the shape of the lens is limited to the form of, or close to, a circle, the exit end face of the light guide must also be shaped into a circular form to suit the shape of the lens. In this way, for a light guide having an annular or crescentric shape, it is difficult to place such an illumination lens.

An approach set forth in Hei 1-198717 brings about phenomena that the amount of light for illuminating an area outside the visual field, because of its diffusion, is increased, while the amount of light for illuminating an area inside the visual field is decreased. Hence, there is a problem in illumination efficiency.

The optical system disclosed in Sho 55-136031, as in Hei 1-198717, raises the problem of increasing the amount of light for illuminating the area outside the visual field because the cylindrical or ball lenses have too strong a refracting power. Moreover, there are problems that the holding of the cylindrical or ball lenses is difficult and that liquids or dust particles are liable to adhere to the cylindrical or ball lenses and the illumination efficiency and light distribution characteristics are degraded because a surface on the exit side of the cylindrical or ball lenses (namely, the entire lens surface from which illumination light emerges) has an irregular shape.

SUMMARY OF THE INVENTION

It is, therefore, a primary object of the present invention to provide an illumination optical system whose outside diameter is reduced to almost the same size as the outside diameter of an illumination source such as a light guide or surface illuminant, favorably maintaining the efficiency of illumination in the visual field.

It is another object of the present invention to provide an illumination optical system which is applicable to light guides or surface illuminants having exit end faces of various shapes, not to speak of a circular one.

In order to achieve the above objects, according to the present invention, the illumination optical system is provided with a diffusion member including a number of nearly spherical members which are diminutive in size and transparent and a transparent medium whose refractive index is higher than that of air and different from that of the nearly spherical members and which holds the nearly spherical members, on the exit end face of a light conducting means for introducing illumination light.

By the above construction, the illumination light leaving the light conducting means such as a light guide or surface illuminant is refracted by the nearly spherical members and the transparent medium. In this way, the divergence of the illumination light is moderately suppressed and a relative amount of illumination light emerging outside the visual field can be reduced. Since the diffusion member is an assembly of the nearly spherical members which are diminutive in size and transparent, the thickness of the diffusion member can be decreased. If the diffusion member is placed immediately close to the light guide, the diameter of the diffusion member can be practically equalized with that of the light guide. This contributes greatly to a reduction in diameter of the endoscope. For the same reason, the diffusion member can be freely shaped and is applicable to light guides of various shapes.

Further, according to the present invention, the illumination optical system is constructed so that the refractive index of the transparent medium is lower than that of the nearly spherical members. By this construction, even if an angle of illumination light incident on the nearly spherical members, of illumination light emerging from the light guide, is large, the illumination light will not undergo total reflection. Consequently, the illumination light can be prevented from arriving outside the visual field because of total reflection.

These and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
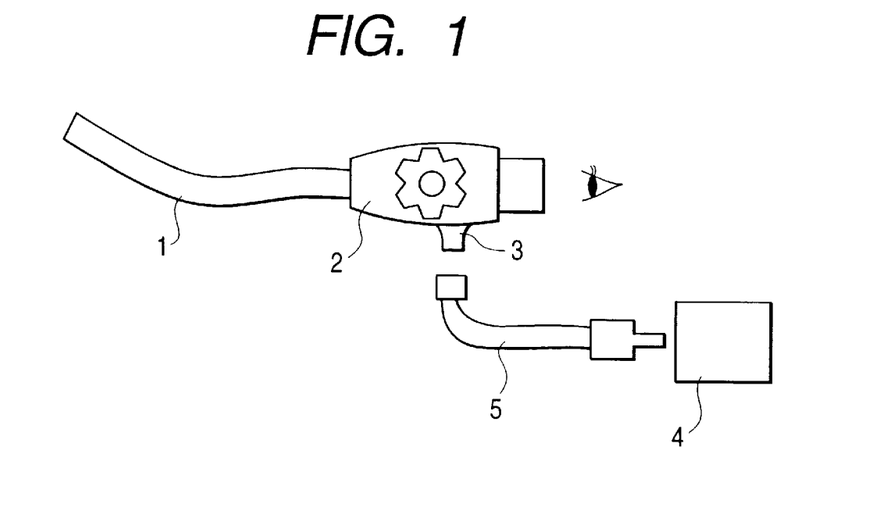
FIG. 1 is a view showing schematically the construction of an endoscope system in the present invention.

Various aspects of the present invention are shown in FIG. 1 through FIG. 13. The endoscope system shown in FIG. 1 includes an endoscope composed of a fine inserting section 1 to be inserted into a cavity in a human body, an operating section 2, and a connecting section 3; and an endoscope illumination device composed of a light source 4 and a light guide cable 5. One end of the light guide cable 5 is connected to the light source 4, and the other is connected to the connecting section 3 of the endoscope. In this way, light from the light source 4 is transmitted to the distal end of the inserting section 1 by the light guide cable 5 and a light guide which is a light conducting means, not shown, encased in the endoscope.

Figure 2A:
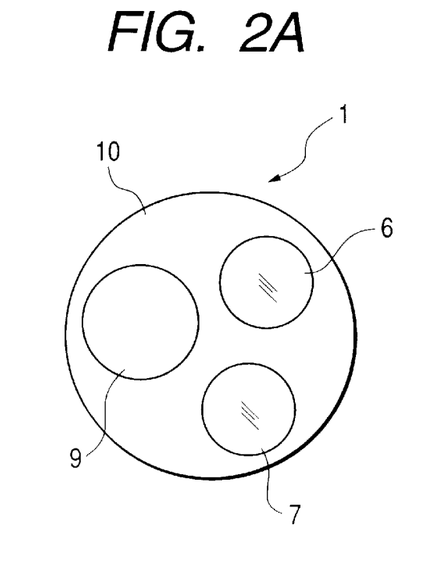
FIGS. 2A and 2B are front and sectional side views, respectively, showing the distal end of an inserting section of an endoscope in FIG. 1.
Figure 2B:
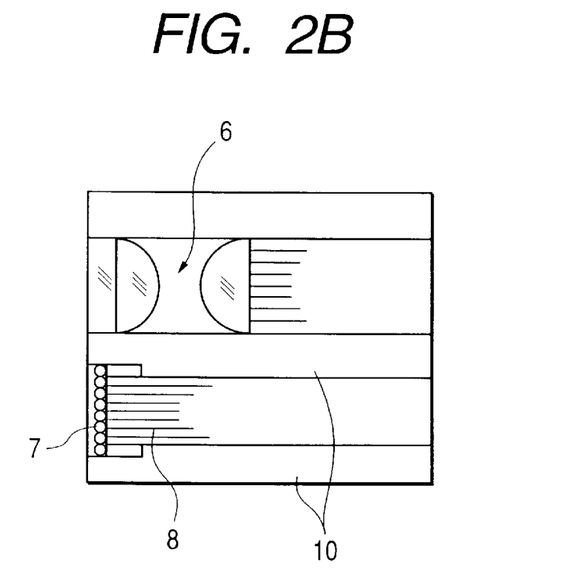

As shown in FIGS. 2A and 2B, the distal end of the inserting section 1 is equipped with an observation optical system 6 and an illumination optical system 7. The light from the light source 4, as mentioned above, is transmitted by a light guide 8 which is the light conducting means, and illuminates an object to be observed, through the illumination optical system 7. An illuminated object is observed through the observation optical system 6. The inserting section 1 is provided with a forceps channel 9 so that treatment tools can be inserted in accordance with applications. Also, reference numeral 10 represents an outer frame of the inserting section 1.

Figure 3:
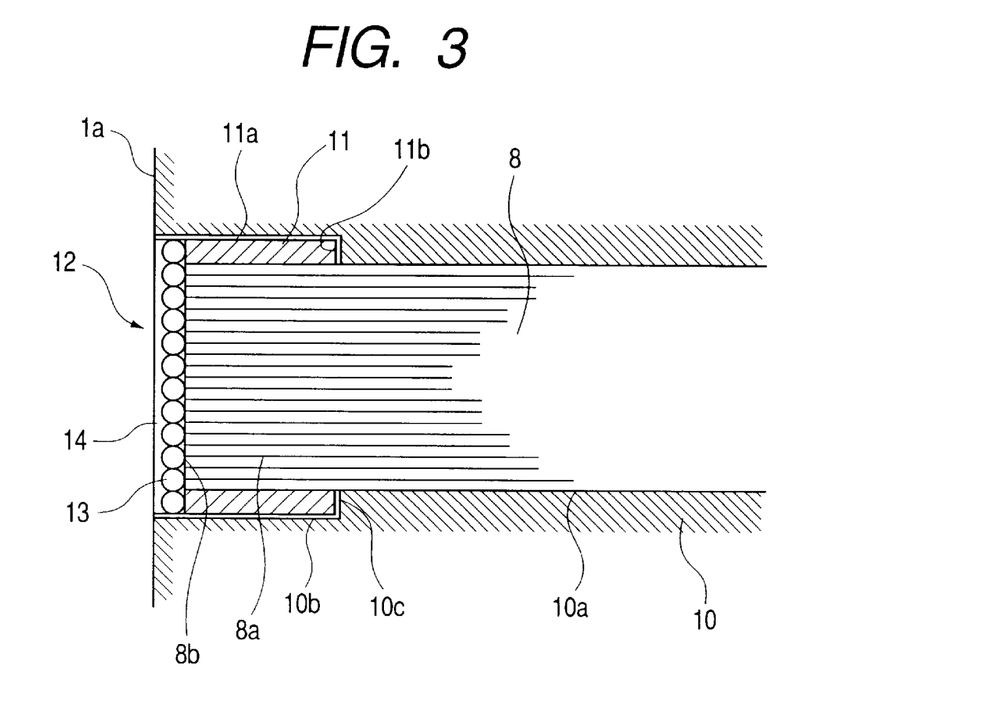
FIG. 3 is a view showing an illumination optical system of the endoscope.

FIG. 3 shows the illumination optical system of the present invention in detail. In the inserting section 1, in order to place the light guide 8 for introducing illumination light, a light guide bore 10a which corresponds to the diameter of the light guide 8 is provided in the outer frame 10 along a longitudinal direction of the inserting section 1. Following the light guide bore 10a, a bore 10b for a light guide base 11 to be described later is provided, in a top end face 1a of the inserting section 1, which has a diameter larger than that of the light guide 8 and a certain depth to suit an outer diameter 11a of the light guide base 11.

At an exit end portion 8a of the light guide 8, on the other hand, the light guide base 11 is wound around the light guide 8. The outer diameter 11a of the light guide base 11, as mentioned above, is equalized to the diameter of the bore 10b for the light guide base 11. Hence, when the light guide 8 is encased in the inserting section 1, an end face 11b of the light guide base 11 strikes an offset portion 10c to position the light guide 8. In FIG. 3, to facilitate the explanation, clearances appear to be provided between the outer diameter 11a of the light guide base 11 and the bore 10b and between the end face 11b of the light guide base 11 and the offset portion 10c. Actually, in either case, they coincide nearly with each other.

Since the length of the light guide base 11 is less than the depth of the bore 10b, it follows that a space is provided between an exit end face 8b of the light guide 8 and the top end face 1a. In this space, a plate-shaped diffusion member 12 is placed. The diffusion member 12 has a number of nearly spherical members 13 which are transparent and diminutive in size and which are surrounded and held by a transparent medium 14. Here, for example, ball lenses are used as the nearly spherical members 13 and a transparent resin is used as the transparent medium 14.

The nearly spherical members 13 are arranged in a close-packed array on the exit end face 8b of the light guide 8 and have a multilayer structure composed of two or three layers, as the case may be. Spaces between the nearly spherical members 13 which are adjacent to one another are charged with the transparent medium 14, by which the positions of respective nearly spherical members 13 are fixed so that the plate-shaped diffusion member 12 is constructed. The thickness of the diffusion member 12 is equalized to a distance from the exit end face 8b of the light guide 8 to the top end face 1a, which has a smooth plane surface with little irregularity.

The diffusion member 12 can be easily fabricated in such a way that, after the nearly spherical members 13 are arranged in an array on the exit end face 8b of the light guide 8, the transparent medium 14, such as a silicon- or fluorine-based resin or adhesive, is poured thereinto and then is cured by means of heat treatment or ultraviolet radiation. Although, in this case, the light guide 8 and the diffusion member 12 are integrally constructed, the diffusion member 12 may be fabricated by itself so that its one end face is brought into contact with the exit end face 8b of the light guide 8 or is cemented thereto with an adhesive. As such, in the case of the integral construction, the nearly spherical members 13 come in contact with the exit end face 8b of the light guide 8, while in the separate construction, they are spaced slightly away from the exit end face 8b.

Figure 4A:
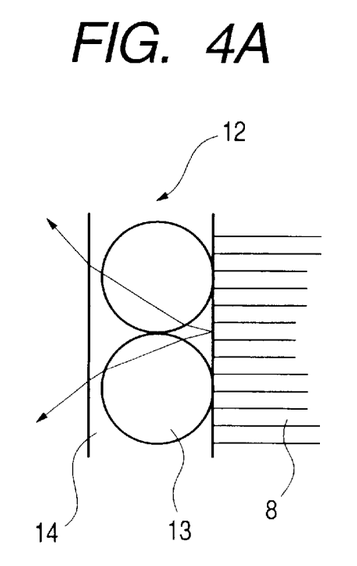
FIGS. 4A and 4B are views showing the behavior of illumination light where nearly spherical members of the illumination optical system are surrounded by a transparent medium and air, respectively.
Figure 4B:
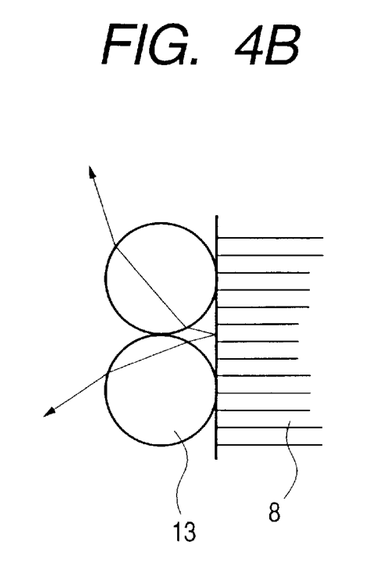

Subsequently, a description is given of the function of the diffusion member 12 with reference to FIGS. 4A and 4B. FIG. 4A shows the diffusion member 12, part of which is enlarged, including the refraction of illumination light where the nearly spherical members 13 are surrounded and held by the transparent medium 14. FIG. 4B shows the refraction of the illumination light where the nearly spherical members 13 are surrounded by air.

The illumination light emerges from the exit end face 8b of the light guide 8 at an angle of emergence (distribution angle) of the illumination light which is governed by the numerical aperture of the light guide 8. The light, when being incident on the transparent medium 14 surrounding the nearly spherical members 13, is refracted at a larger angle than the distribution angle of the light guide 8 by a refracting action. In this way, a wide area can be illuminated in contrast with the case of the light guide 8 alone. Since, however, an angle of refraction is suppressed by the transparent medium 14, it is avoidable that the light is refracted at a larger angle than is necessary, compared with the case of air.

After that, the illumination light is incident on the nearly spherical members. At this time, by a refracting action due to a difference in refractive index between the nearly spherical members 13 and the transparent medium 14, the light is deflected at an angle larger than that where it emerges from the exit end face 8b of the light guide 8. Consequently, an angle of illumination is obtained which is larger than the angle of emergence (distribution angle) of the illumination light governed by the numerical aperture of the light guide 8.

The illumination light passing through the nearly spherical members 13 emerges again toward the transparent medium 14. In contrast with the case where the light emerges directly from the nearly spherical members 13 into air (FIG. 4B), the refracting power of the nearly spherical members 13 is weakened because the difference in refractive index between the nearly spherical members 13 and their surrounding material is small. In this way, the angle of emergence is held small and the illumination light is not deflected at a larger angle than is necessary. As a result, the relative amount of illumination light illuminating the area outside the visual field of the observation optical system can be reduced, and illumination with high efficiency can be obtained.

For refractive indices of respective materials constituting the diffusion member 12, materials with refractive indices ranging from about 1.5 to 2.0, selected from among ordinary optical materials, are used for the near spherical members 13, and materials with refractive indices ranging from about 1.3 to 1.6 are used for the transparent medium 14 which is a silicon- or fluorine-based resin or adhesive.

The nearly spherical members 13 and the transparent medium 14 are used by combining materials of different refractive indices selected from the above ranges. Here, when the nearly spherical members 13 are higher in refractive index than the transparent medium 14, a positive refracting power is obtained, while when it is lower, a negative refracting power is produced. In either case, illumination can be provided at a larger angle than the distribution angle of the light guide 8.

However, where the nearly spherical members 13 are lower in refractive index than the transparent medium 14, illumination light with a relatively large angle of incidence, of the illumination light incident on the nearly spherical members, undergoes total reflection, and this totally reflected light sometimes arrives outside the visual field of the observation optical system. In view of the fact that the nearly spherical members 13 range in refractive index from about 1.5 to 2.0, where the nearly spherical members 13 are lower in refractive index than the transparent medium 14, the range of the selection of material is narrowed. As such, it is desirable that the transparent medium 14 is lower in refractive index than the nearly spherical members 13.

When ball lenses are used as the nearly spherical members 13, the radiation area of the illumination light is governed by the numerical aperture of the light guide 8 and the refractive indices of the ball lenses and the transparent medium 14, but does not depend on the size of the ball lenses, and thus ball lenses of arbitrary, identical diameters can be selected. On the other hand, the thickness of the diffusion member 12 depends on the size of the ball lenses. Thus, ball lenses which are small in diameter are selected and thereby the diffusion member 12 of very small thickness can be constructed. In this way, the illumination optical system of the present invention utilizes a plurality of refractions produced by a combination of the nearly spherical members 13 and the transparent medium 14 which lie in a minute region like the diffusion member 12, and provides illumination such that a small divergence angle of light is converted into a larger divergence angle and there is little difference in amount of light between the center and the periphery in a predetermined area.

Today, the ball lenses are made in sizes of several micrometers (μm), and the use of such ball lenses leads to an advantage in compactness. However, there is no problem even when ball lenses which are larger in diameter, for example, on the order of 200 micrometers in diameter, are used. Specifically, the light guide 8 is provided with the light guide base 11, and thus even though the ball lenses used in the diffusion member 12 are on the order of 200 micrometers in diameter, they will be arranged even at the position of the light guide base 11 if the outer diameter of the diffusion member 12 is practically equalized with that of the light guide base 11. Hence, the illumination light emerging from the periphery of the light guide 8 also travels toward the object, without vignetting, by virtue of the ball lenses arranged at the position of the light guide base 11. In this way, even though the ball lenses of the order of 200 micrometers are used, the diffusion member 12 can be rendered smaller in outer diameter than a conventional illumination lens.

Since the diffusion member 12 in the illumination optical system of the present invention is constructed as mentioned above, it is possible to illuminate a wide area at a larger angle than the distribution angle of the light guide 8, as well as an area suitable for the visual field of the observation optical system, without producing a conventional problem of enlarging the outside diameter (diameter and thickness) of the illumination optical system in accordance with a tendency to radiate illumination light at a wide angle. Moreover, compactness of the illumination optical system, which allows the diameter of the inserting section of the endoscope to be diminished, brings about the effect of reducing pain caused when the endoscope is inserted in the human body.

Figure 5:
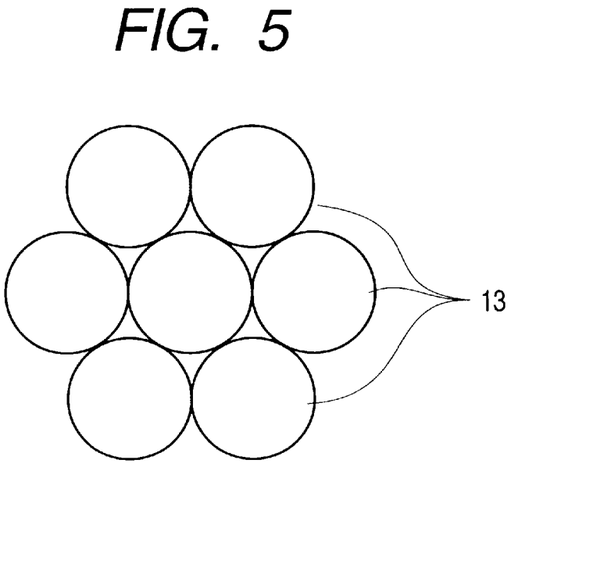
FIG. 5 is a view showing the nearly spherical members arranged in a hexagonal close-packed array.

In the present invention, the nearly spherical members 13 are closely arranged in an array, and it is desirable that they are arranged in a hexagonal close-packed array as illustrated in FIG. 5. This is because the arrangement of the hexagonal close-packed array increases the relative amount of illumination light passing through the nearly spherical members 13 via the light guide 8, with the result that a greater deal of illumination light is refracted and the distribution angle can be efficiently increased. Although, in FIG. 5, the nearly spherical members 13 come in contact with one another, they can be spaced away from one another to such an extent that distribution characteristics are not degraded.

Figure 6:
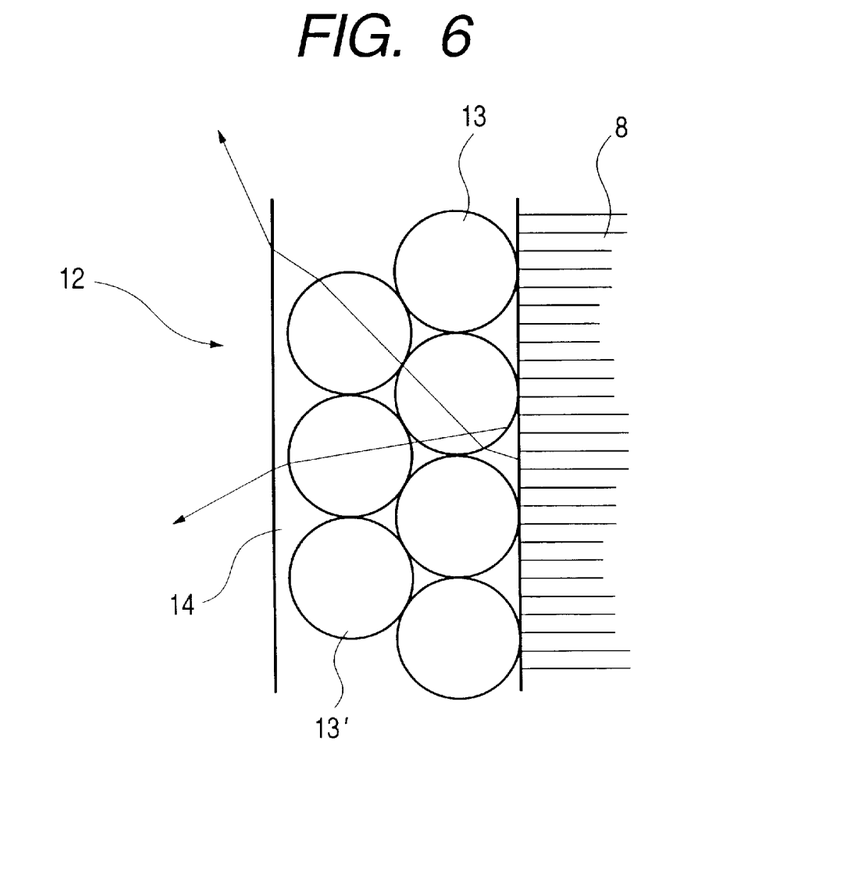
FIG. 6 is a view showing the nearly spherical members arranged in two overlapping layers.

Moreover, the nearly spherical members may have a multilayer arrangement such that they are superimposed along the optical axis. Specifically, the nearly spherical members, as depicted in FIG. 6, are superimposed and arranged in two layers, and thereby the illumination light which is too strongly refracted by the nearly spherical members 13 of a first layer can be refracted in a reverse direction by nearly spherical members 13' of a second layer. As such, the relative amount of illumination light arriving outside the visual field of the observation optical system is decreased and the illumination light can be widely distributed with high efficiency. Even though part of the illumination light has passed through one of spaces between the nearly spherical members 13 of the first layer, it would be refracted by any of the nearly spherical members 13' of the second layer, and thus the illumination light can be widely distributed.

Figure 7:
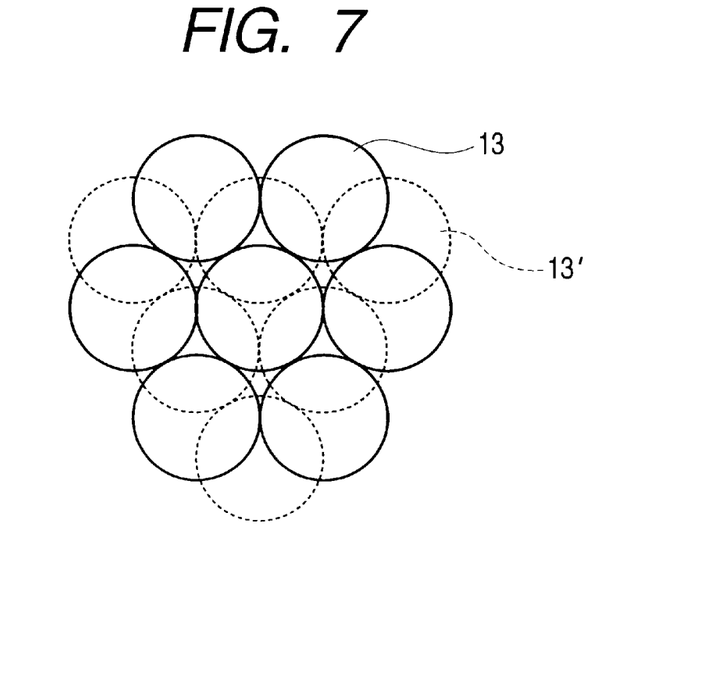
FIG. 7 is a view showing the nearly spherical members arranged in two layers, each with a hexagonal close-packed array.
Figure 8:
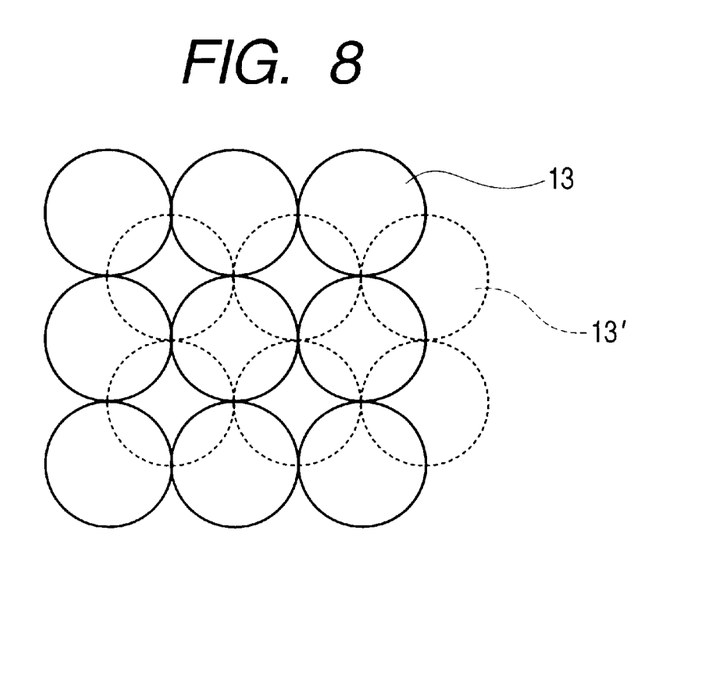
FIG. 8 is a view showing the nearly spherical member arranged in two layers, each with a tetragonal close-packed array.

In order to closely arrange the nearly spherical members 13 and 13', it is favorable to arrange them in a hexagonal close-packed array as described above. However, when they are arranged in two layers, each with a hexagonal close-packed array, as shown in FIG. 7, spaces are produced through the layers, depending on a positional relationship between them, and the effect of superimposing the two layers cannot be completely brought about. Thus, where the nearly spherical members are arranged in two layers, it is desirable that the nearly spherical members of each layer, as shown in FIG. 8, are arranged in a tetragonal close-packed array so that the nearly spherical members 13' of the second layer are superimposed on the spaces produced between the nearly spherical members 13, adjacent to one another, of the first layer. When the arrangement is made as shown in FIG. 8, the illumination light passing through one of the spaces between the nearly spherical members 13 of the first layer necessarily travels through any of the nearly spherical members 13' of the second layer. Hence, the relative amount of illumination light which does not pass through the nearly spherical members 13 and 13' is decreased, while a greater deal of illumination light is refracted and can be widely distributed with higher efficiency.

Figure 9:
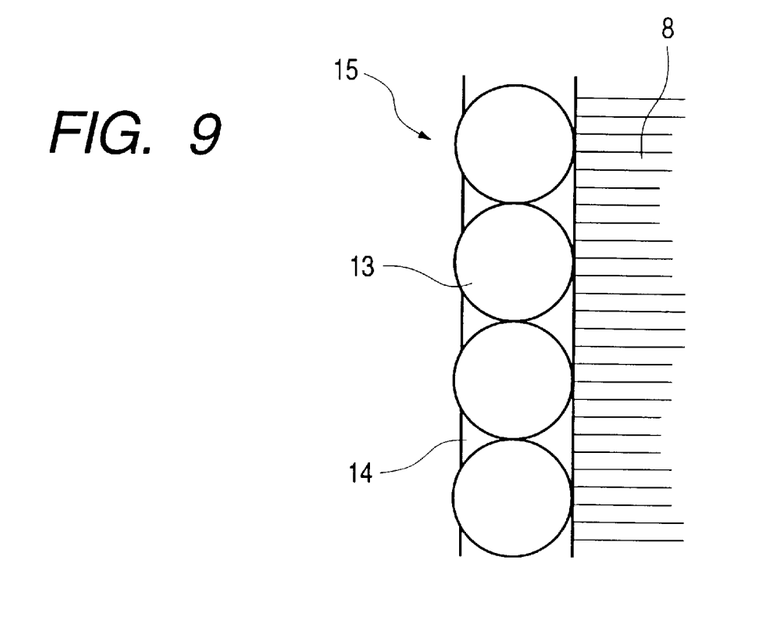
FIG. 9 is a view showing a diffusion member whose surface has a slightly irregular shape.

Since, as mentioned above, the nearly spherical members 13 are held in a state that they are surrounded by the transparent medium 14, the holding of the nearly spherical members 13 is easy compared with the case where the near spherical members 13 are arranged and held in air. The nearly spherical members 13 are surrounded by the transparent medium 14 and are shaped into a plate-like form as a whole, and thus the diffusion member 12 has a flat surface. As a result, the surface is practically free of adhesion or residue of dust particles or liquids, and even though they adhere, the surface can be easily wiped clean. However, the surface of the diffusion member need not necessarily be completely flat, and as shown in FIG. 9, a diffusion member 15 may be constructed so that the nearly spherical members 13 are practically surrounded by the transparent medium 14 and individual surfaces of the nearly spherical members 13 project slightly from the surface of the transparent medium 14. In this case also, the nearly spherical members 13 are firmly held by the transparent medium 14 without any structural problem, the adhesion of dust particles is not virtually produced, and the distribution of illumination light is not adversely affected.

Figure 10:
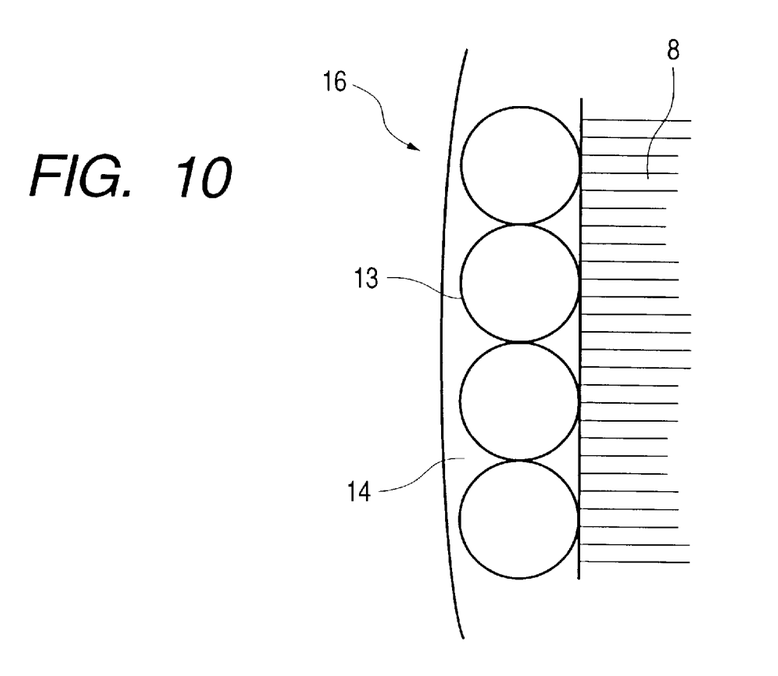
FIG. 10 is a view showing the diffusion member whose surface is slightly curved.

For the shape of a diffusion member, for example, as shown in FIG. 10, a diffusion member 16 may be constructed which has a slightly curved surface. By providing such a curved surface, a refracting action due to the curved surface can be utilized for improving the distribution of illumination light.

Figure 11:
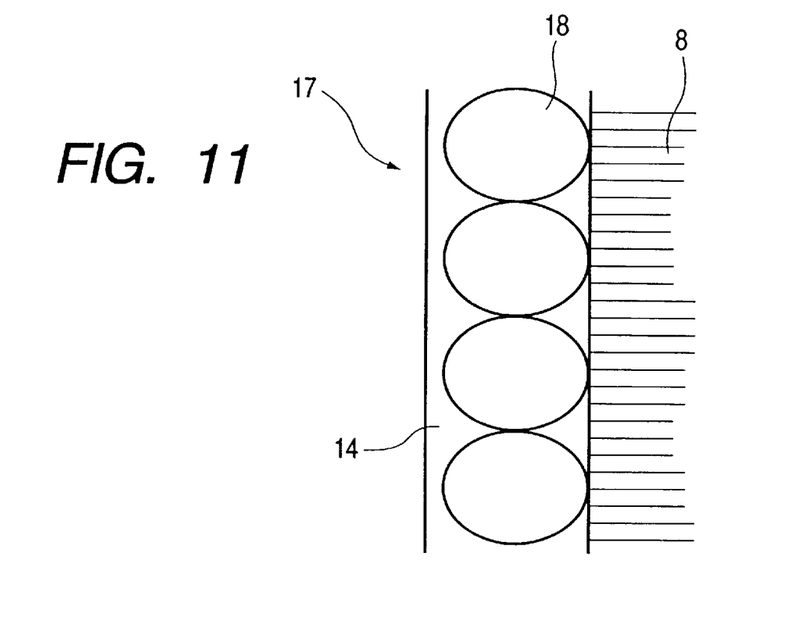
FIG. 11 is a view showing a case where elliptical lenses are used as the nearly spherical members.

In the disclosure so far, the ball lenses have been used as the nearly spherical members, but as shown in FIG. 11, even when a diffusion member 17 is comprised of elliptical lenses 18 and the transparent medium 14, the distribution of illumination light can be made favorable as in the case of the ball lenses.

The diffusion member, which is constructed with an assembly of the nearly spherical members of diminutive size, can be shaped into various forms. In this way, the diffusion member of the present invention, in contrast with the fact that a conventional illumination lens is applicable only to a light guide of circular cross section, can be used for light guides of various cross sections, such as annular, elliptical, and crescentric shapes, not to speak of a circular one. Thus, even where a light conducting means other than the light guide, for example, a surface illuminant is used, the diffusion member can be easily fabricated to suit the shape of its light emission surface.

Figure 12:
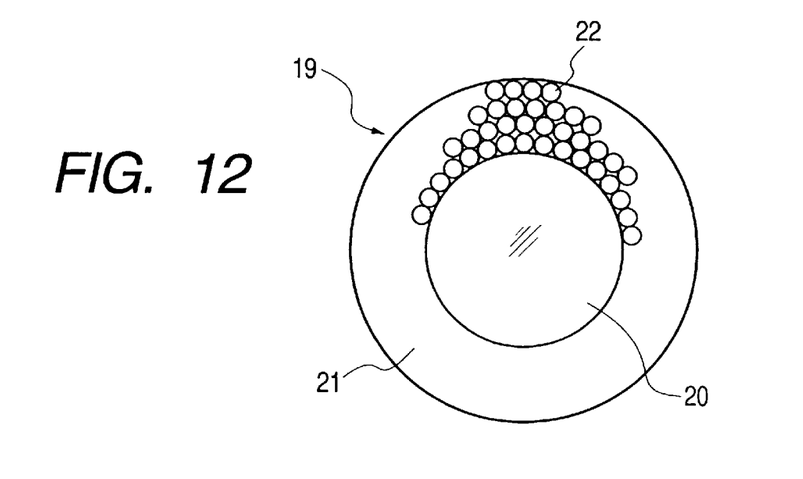
FIG. 12 is a view showing a case where the diffusion member is shaped into an annular form.

FIG. 12 shows the distal end of an inserting section 19 of a rigid endoscope. The rigid endoscope is in general constructed only with the observation optical system and the illumination optical system, and the inserting section 19 thereof has an observation optical system 20 placed at the center. In this way, an illumination optical system 21 assumes an annular shape such as to surround the observation optical system 20, and thus it is difficult to place the conventional illumination lens. However, if the diffusion member used in the illumination optical system of the present invention is applied thereto, it can be shaped to suit the light guide. Hence, even with the rigid endoscope, the distribution angle can be efficiently increased. Also, in FIG. 12, nearly spherical members 22 of identical diameters are used to construct the illumination optical system 21 of annular shape.

Figure 13:
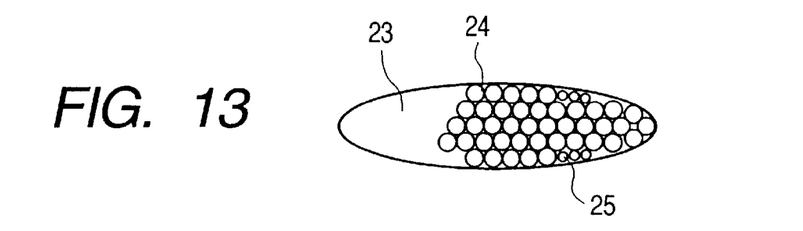
FIG. 13 is a view showing a case where the diffusion member is shaped into an elliptical form.

FIG. 13 shows a case where an illumination optical system 23 has an elliptical shape. Since the use of the nearly spherical members of identical diameters brings about spaces between their peripheries, the diffusion member of the illumination optical system 23 is constructed with nearly spherical members 24 and 25 of different diameters so that spaces between the nearly spherical members 24 which are relatively large in diameter are filled with the nearly spherical members 25 which are smaller in diameter.

As described above, in the diffusion member used in the illumination optical system of the present invention, one layer can be constructed with the nearly spherical members of identical diameters A or different diameters A, B, C, . . . , etc.

Where a multilayer is built up, it can be constructed by arbitrarily combining structures relative to the above-mentioned one layer. For example, this involves the following:
1. All layers are constructed with the nearly spherical members of identical diameters A.
2. The first layer is constructed with the nearly spherical members of identical diameters A, while the second layer is constructed with the nearly spherical members of identical diameters B which are different from the diameters A in the first layer.
3. The first layer is constructed with the nearly spherical members of identical diameters A, while the second layer is constructed with the nearly spherical members of different diameters A. B, C, . . . , etc.

In accordance with the embodiments, the present invention will be explained in more detail below.

The embodiments in the illumination optical system of the present invention are shown below. Each of the embodiments uses a light guide in which hundreds of single fibers, each having a diameter of 30 micrometers and a core diameter of 27 micrometers, are bundled to have an outside diameter of about 1 millimeter. Also, the light distribution characteristics of the embodiments are plotted in FIGS. 14 and 15.

First embodiment

The illumination optical system of the first embodiment in the present invention is designed so that ball lenses, each with a diameter of 100 micrometers and a refractive index of 1.51633, are arranged in a single layer with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a dotted line (1) in FIG. 14.

Second embodiment

The illumination optical system of the second embodiment in the present invention is designed so that ball lenses, each with a diameter of 100 micrometers and a refractive index of 1.6, are arranged in a single layer with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a dotted line (2) in FIG. 14.

Third embodiment

The illumination optical system of the third embodiment in the present invention is designed so that ball lenses, each with a diameter of 50 micrometers and a refractive index of 1.7, are arranged in a single layer with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a dotted line (3) in FIG. 14.

Fourth embodiment

The illumination optical system of the fourth embodiment in the present invention is designed so that ball lenses, each with a diameter of 50 micrometers and a refractive index of 1.8, are arranged in a single layer with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a chain line (4) in FIG. 14.

Fifth embodiment

The illumination optical system of the fifth embodiment in the present invention is designed so that ball lenses, each with a diameter of 100 micrometers and a refractive index of 1.51633, are arranged in two layers, each with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a broken line (5) in FIG. 15.

Sixth embodiment

The illumination optical system of the sixth embodiment in the present invention is designed so that ball lenses, each with a diameter of 100 micrometers and a refractive index of 1.62004, are arranged in two layers, each with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a broken line (6) in FIG. 15.

Seventh embodiment

The illumination optical system of the seventh embodiment in the present invention is designed so that ball lenses, each with a diameter of 50 micrometers and a refractive index of 1.698, are arranged in two layers, each with a hexagonal close-packed array, as the nearly spherical members, on the exit end face of a light guide with a numerical aperture of 0.66, and are surrounded by a silicon-based, transparent resin with a refractive index of 1.41 which constitutes the transparent medium. The light distribution characteristics in this case are indicated by a broken line (7) in FIG. 15.

Figure 14:
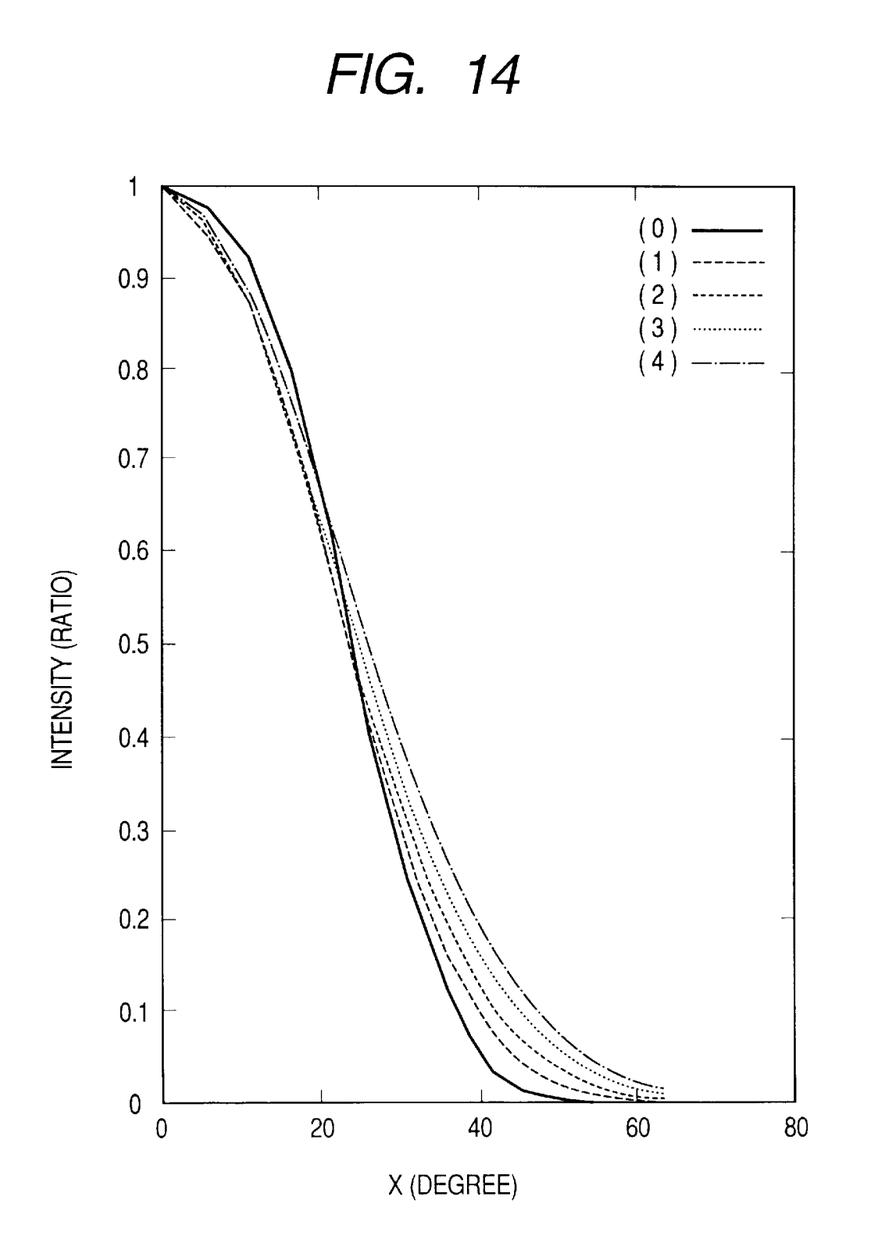
FIG. 14 is a diagram showing light distribution characteristics of the illumination optical system in first through fourth embodiments.
Figure 15:
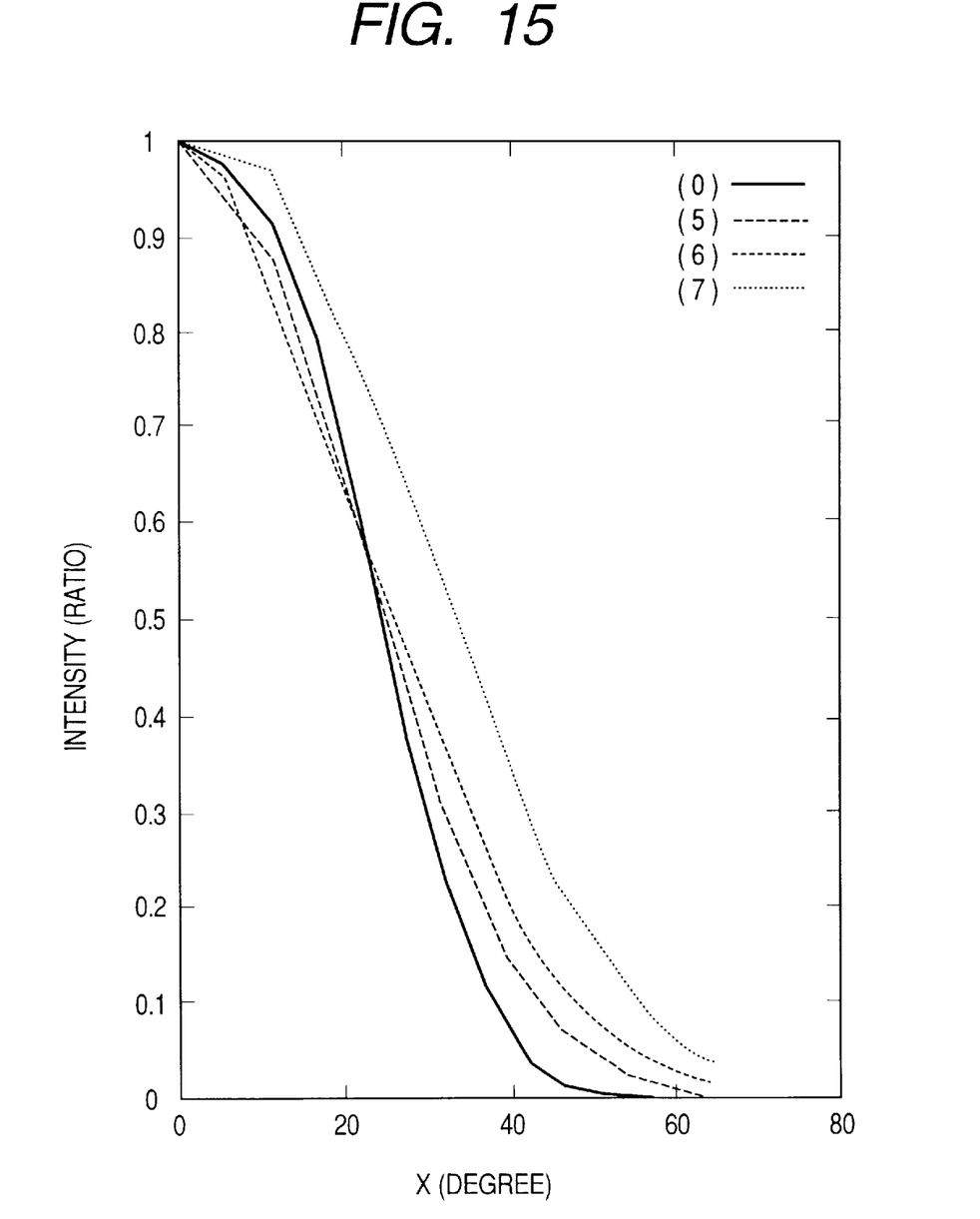
FIG. 15 is a diagram showing light distribution characteristics of the illumination optical system in fifth through seventh embodiments.

As mentioned above, the light distribution characteristics in the first through fourth embodiments are plotted in FIG. 14 for the case where the nearly spherical members are arranged in a single layer. The light distribution characteristics in the fifth through seventh embodiments are plotted in FIG. 15 for the case where the nearly spherical members are arranged in two layers. Also, in each of FIGS. 14 and 15, a solid line (0) represents the light distribution characteristics of the light guide alone.

As will be obvious from FIG. 14, in the embodiments of the present invention, the intensity ratio of light close to the center, in contrast with the case of the light guide alone denoted by the solid line (0), is somewhat low (namely, the visual field becomes relatively dark). However, in a region which is large in angle, it is seen that the intensity ratio is high (namely, the visual field becomes relatively bright) and the performance of illumination in the periphery of an observation field is improved. The same holds for the case of FIG. 15, and especially in the seventh embodiment, it is found that the intensity ratio is increased in the entire region of the observation field and the illumination performance as a whole, is markedly improved.

What is claimed is:

1. An illumination optical system comprising:
   a light conducting means for introducing illumination light; and
   a diffusion member disposed on an exit end face of said light conducting means, said diffusion member including:
     a number of nearly spherical members which are diminutive in size and transparent; and
     a transparent medium whose refractive index is higher than a refractive index of air and different from a refractive index of said nearly spherical members, said transparent medium holding said nearly spherical members in such a manner that light emergent from the exit end face of said light conducting means is incident on said nearly spherical members after being transmitted through said transparent medium,
   wherein said nearly spherical members are closely arranged in at least one layer on the exit end face of said light conducting means.

2. An illumination optical system, comprising:
   a light conducting means for introducing illumination light; and
   a diffusion member disposed on an exit end face of said light conducting means, said diffusion member including:
     a number of nearly spherical members which are diminutive in size and transparent; and
     a transparent medium whose refractive index is higher than a refractive index of air and different from a refractive index of said nearly spherical members,
   wherein said nearly spherical members are closely arranged in at least one layer on the exit end face of said light conducting means, and
   wherein said nearly spherical members includes a first layer of said nearly spherical members closely arranged on the exit end face of said light conducting means and a second layer of said nearly spherical members closely arranged, superimposed on said first layer.

3. An illumination optical system according to claim 1, wherein said nearly spherical members are closely arranged on the exit end face of said light conducting means to form a hexagonal close-packed array.

4. An illumination optical system according to claim 1, 2 or 3, wherein the refractive index of said transparent medium is lower than the refractive index of said nearly spherical members.

5. An illumination optical system according to claim 4, wherein said nearly spherical members are ball lenses.

6. An illumination optical system according to claim 5, wherein said ball lenses have an outside diameter of 200 micrometers or less.

7. An illumination optical system according to claim 4, wherein said diffusion member has a plate-like shape.

8. An illumination optical system comprising:
a diffusion member for receiving light from an illumination light source, said diffusion member including:
a number of nearly spherical members which are diminutive in size and transparent; and
a transparent medium whose refractive index is higher than a refractive index of air and different from a refractive index of said nearly spherical members, said transparent medium holding said nearly spherical members in such a manner that light emanating from the illumination light source is incident on said nearly spherical members after being transmitted through said transparent medium,
wherein the refractive index of said transparent medium is lower than the refractive index of said nearly spherical members.

9. An endoscope, comprising:
an observation optical system;
a light source; and
an illumination optical system disposed proximate to said observation optical system and said light source;
wherein said illumination optical system comprises:
a light guide having a light receiving end and a light emitting end, said light receiving end being disposed in a path of light emitted from said light source, and
a diffusion member joined to said light emitting end of said light guide,
said diffusion member comprising a plurality of refracting members having a first refractive index and a transparent medium having a second refractive index,
said plurality of refracting members being substantially embedded in said transparent medium, and
said first refractive index being different from said second refractive index.

10. An endoscope according to claim 9, wherein said second refractive index of said transparent medium is less than said first refractive index of said plurality of refracting members.

11. An endoscope according to claim 9, wherein said plurality of refracting members are substantially spherical members.

12. An illumination optical system comprising:
a light guide having a light receiving end and a light emitting end, and
a diffusion member joined to said light emitting end of said light guide,
wherein said diffusion member comprises a plurality of refracting members having a first refractive index and a transparent medium having a second refractive index,
said plurality of refracting members being substantially embedded in said transparent medium,
said first refractive index being different from said second refractive index, and wherein said second refractive index of said transparent medium is less than said first refractive index of said plurality of refracting members.

13. An illumination optical system comprising:
a light conducting means for introducing illumination light; and
a diffusion member disposed on an exit end face of said light conducting means, said diffusion member including:
a number of nearly spherical members which are diminutive in size and transparent; and
a transparent medium whose refractive index is higher than a refractive index of air and different from a refractive index of said nearly spherical members, said transparent medium holding said nearly spherical members in such a manner that light emergent from the exit end face of said light conducting means is incident on said nearly spherical members after being transmitted through said transparent medium,
wherein the refractive index of said transparent medium is lower than the refractive index of said nearly spherical members.

14. An illumination optical system according to claim 13, wherein said nearly spherical members are ball lenses.

15. An illumination optical system according to claim 13, wherein said diffusion member has a plate-like shape.

* * * * *